United States Patent [19]

Sick et al.

[11] Patent Number: 4,632,546
[45] Date of Patent: Dec. 30, 1986

[54] GROOVED SURFACE DEFECT DETECTION APPARATUS

[75] Inventors: Erwin Sick; Christoph Schenk, both of Icking, Fed. Rep. of Germany

[73] Assignee: Erwin Sick GmbH Optik-Elektronik, Waldkirch, Fed. Rep. of Germany

[21] Appl. No.: 599,890

[22] Filed: Apr. 13, 1984

[30] Foreign Application Priority Data

Apr. 22, 1983 [DE] Fed. Rep. of Germany ....... 3314620

[51] Int. Cl.⁴ ............................................. G01N 21/89
[52] U.S. Cl. .................................. 356/237; 356/369; 250/562
[58] Field of Search ............... 356/237, 239, 369, 430, 356/431, 445, 446; 250/550, 562, 563, 572

[56] References Cited

U.S. PATENT DOCUMENTS

| | | | |
|---|---|---|---|
| 3,474,254 | 10/1969 | Piepenbrink et al. | 356/430 X |
| 3,790,286 | 2/1974 | Kraus | 356/369 |
| 3,821,557 | 6/1974 | Lipke | 356/431 X |
| 4,118,127 | 10/1978 | Klein et al. | 356/237 X |
| 4,180,830 | 12/1979 | Roach | 356/237 X |
| 4,197,011 | 4/1980 | Hudson | 250/550 X |
| 4,284,357 | 8/1981 | Kudo | 356/431 |
| 4,352,564 | 10/1982 | Roach | 356/237 X |
| 4,395,122 | 7/1983 | Southgate et al. | 356/237 |

Primary Examiner—Vincent P. McGraw
Assistant Examiner—S. A. Turner
Attorney, Agent, or Firm—Townsend and Townsend

[57] ABSTRACT

Figure 1:
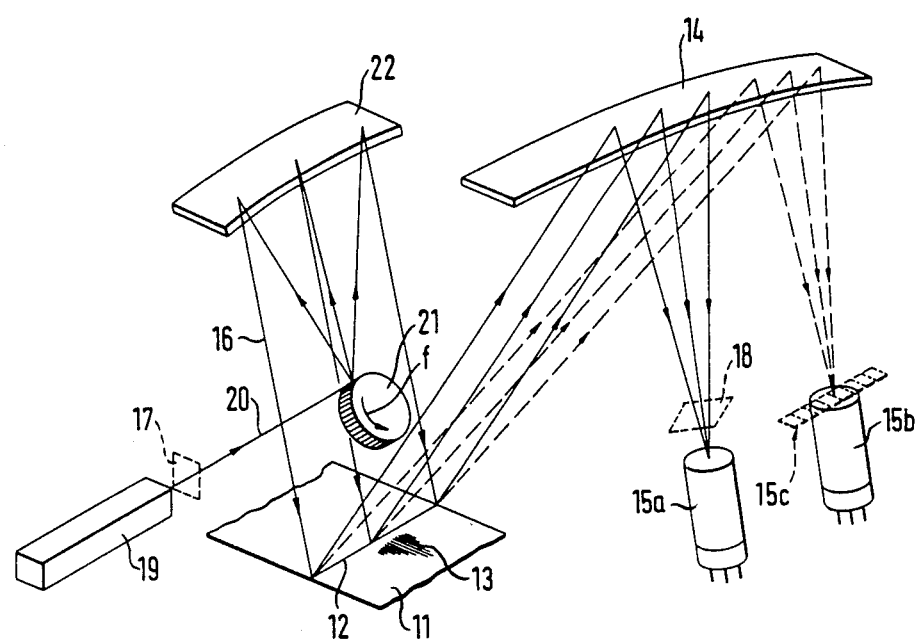

A fault detecting apparatus for flat articles generates a line of light on the article which is imaged onto a photoreceiver via an optical system having cylindrical imaging characteristics. For use with an article 11 having light diffracting characteristics the line of light 12 is arranged substantially at right angles to the structure 13 which causes the light diffraction. The optical system 14 having cylindrical imaging characteristics detects, apart from the zero order at least also the first diffraction order of the light leaving the article. The light of the first diffraction order is also imaged onto its own photoreceiver (FIG. 1).

9 Claims, 2 Drawing Figures

GROOVED SURFACE DEFECT DETECTION APPARATUS

The invention relates to fault detection apparatus for flat articles wherein a line of light is generated on the article and is imaged onto a photoreceiver in an optical system having cylindrical imaging characteristics.

Only one photoreceiver is normally used in fault detection apparatus of this kind. If faults are present in the material the photoreceiver transmits a fault signal as a result of the additional deflection of light which takes place at the faults. If necessary, two or more photoreceivers can also receive light by exploiting the scattering angle for the light at the article, in order to be able to detect faults of different natures.

The object underlying the invention is to provide fault detection apparatus of the initially named kind which can be used to obtain more comprehensive information concerning faults with articles which have light diffracting characteristics. It is a particular object of the invention to provide fault detection apparatus which is suitable for finding faults with so-called laser disks which have very narrow grooves, the spacing of which is of the order of magnitude of the wavelength of visible light, so that diffraction effects occur when using visible or infrared light.

In order to satisfy these objects the invention provides a fault detecting apparatus which is characterised in that the line of light is arranged substantially at right angles to the structure producing the light diffraction; in that the optical system detects at least the first diffraction order of the light leaving the article in addition to the zero order; and in that the light from the first and optionally further diffraction orders is imaged onto its own associated photoreceiver. The article is in particular a record which is to be scanned by a laser beam with the light beam extending radially over the record. The invention is thus especially suited to the detection of faults in articles which have a substantially linear, extended, diffracting structure.

It is particularly advantageous if the line of light is formed by a moving beam of light which is periodically movable to and fro. The moving beam can, in the first instance be generated by a mirror wheel illuminated by a laser.

In order to obtain a good yield of light the transmitted light should fall on the article and be reflected to the optical system at the angle of reflection. The light diffraction then takes place in a plane at right angles to the plane of reflection.

The principal purpose of the apparatus of the invention is that several photoreceivers can receive light which signifies different faults. For this purpose polarised light can for example be used, with an analyser being arranged in front of one of the photoreceivers but not in front of the other. The one photoreceiver thus primarily registers depolarising material faults whereas the other photoreceiver can respond to other faults.

The optical system having cylindrical imaging characteristics can consist of a single strip-like cylindrical mirror which should be made sufficiently long to receive at least two diffraction orders.

In accordance with a further embodiment the optical system can however also consist of as many strip-like cylindrical lenses as there are photoreceivers.

Figure 2:
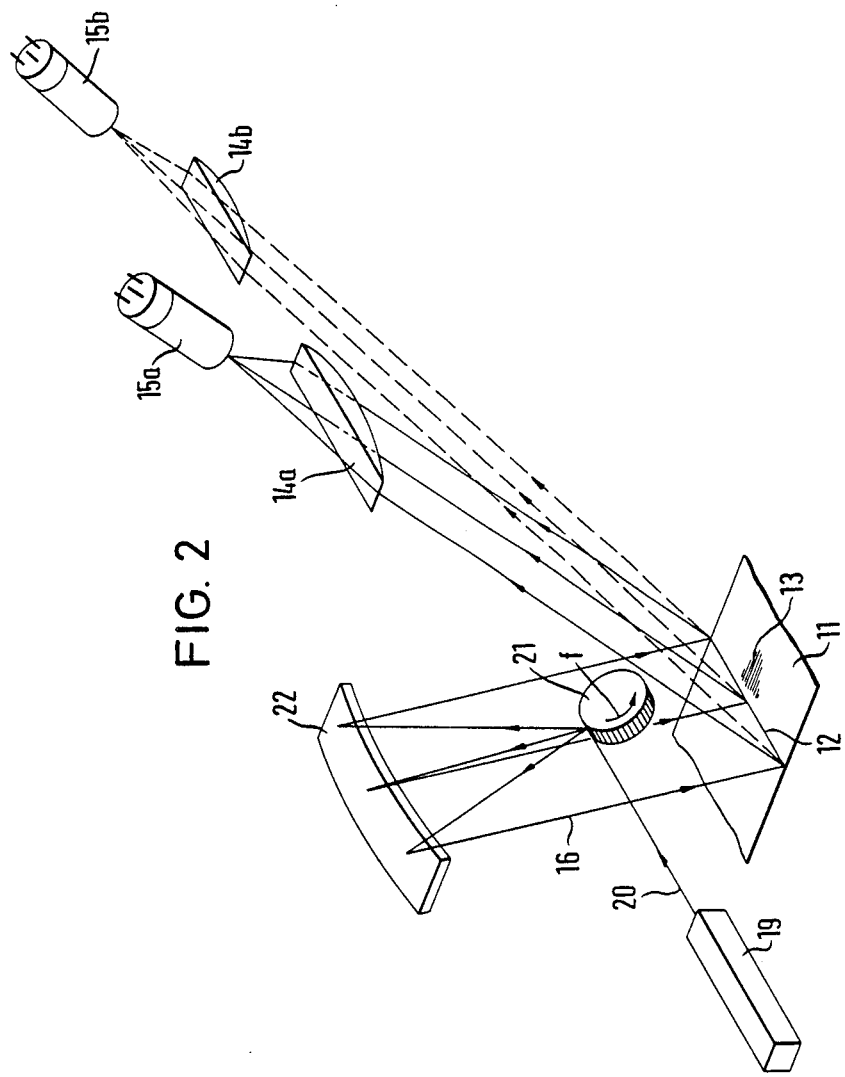

The invention will now be described in the following by way of example and with reference to the drawing which shows:

FIG. 1 a schematic perspective illustration of a first embodiment of the fault detecting apparatus of the invention, and FIG. 2 a perspective reproduction of a further embodiment.

As seen in FIG. 1 a tightly bundled light beam 20 leaving a laser 19 falls on a mirror wheel 21 the reflective periphery of which is arranged at the focal point of a strip-like concave transmitting mirror 22. The light reflected from the concave mirror is displaced relative to the mirror wheel sufficiently that it can pass by the mirror wheel and reach the surface of a flat article 11 whereby a line or bar of light 12 is generated by the mirror wheel which is rotating in the sense of the arrow f. The line of light 12 extends at right angles to a linear diffraction structure 13 present on the surface of the article 11 which can for example consist of the microgrooves of a laser disk.

The moving beam reflected by the concave mirror 22 impinges, in accordance with FIG. 1, obliquely on the surface of the article 11 so that, for a substantially reflecting surface it is reflected at the angle of reflection by the article 11. A strip-like receiving concave mirror 14 is arranged spaced apart from the article 11 at this angle and forms an optical system having cylindrical imaging characteristics.

The zero reflection order illustrated in full lines is concentrated on a first photoreceiver 15a, which is constructed as a photomultiplier. In other words the surface of the mirror wheel 21 is imaged via the concave mirrors 22, 14 onto the photomultiplier 14a. As a result of the diffraction structure 13 light is however also deflected to both sides into the first diffraction order. FIG. 1 only shows the one diffraction order which falls on the cylindrical mirror 14 as a result of a suitable construction of the latter, and which is deflected by this cylindrical mirror 14 into a second photoreceiver 15b, which is likewise constructed as a photomultiplier. In this manner two different photoreceivers are available for receiving the reflected light.

By arranging, by way of example, a polariser 17 in the laser beam 20 and an analyser 18 in front of the photoreceiver 15a the photoreceiver 15a can be made to respond to depolarising faults whereas the receiver 15b responds to other faults. The zero order is shown in full lines in FIG. 1 the first diffraction order is however illustrated in broken lines. The ratio of the wavelength of the laser beam to the grid constant of the grooves of linear diffraction structure 13 of flat article 11 is preferably chosen to generate at most zero, first and second diffraction orders.

In FIG. 2 the same reference numerals are used to designate parts which have counter-parts in FIG. 1.

In distinction to FIG. 1 the optical system having cylindrical imaging characteristics consists in this embodiment of two separate cylindrical lenses 14a, 14b which receive the zero and first diffraction orders of the light leaving the light beam 12 and concentrate them onto the photoreceivers 15a and 15b respectively.

The invention thus provides a beam division for articles having a diffraction structure without a special beam divider being required for this purpose.

The gathering system 14, 14a, 14b could be dispensed with if the article being tested has small dimensions in the scanning direction and if a large area receiver (for example rectangular photomultiplier) is simultaneously used.

FIG. 1 also indicates in broken lines, the location of the first diffraction order, a line-like photoreceiver arrangement 15c which can be provided in place of the photoreceiver 15b and which consists of a plurality of individual photoreceivers arranged alongside one another. In this manner lateral displacements of the first diffraction order can be detected which are a measure for changes of the periodicity of the periodic diffraction structure 13.

If the invention is used for monitoring the grooves or lines which occur during a turning process then the turning process can be monitored by means of this embodiment.

The articles to be investigated with the apparatus of the invention can for example be laser discs, video discs, computer storage discs and also surfaces which are machined in a turning machine.

It will be understood that the line of light does not need to extend across the full width of the article being examined although it should extend over a substantial number of elements of the diffracting structure. The scanning of the line of light across the full width of the article ensures that faults anywhere on the surface of the article are detected. It will also be appreciated that the term "optical system with cylindrical imaging characteristics" is not restricted to systems with purely cylindrical imaging characteristics but also extends to other optical systems which will produce a line focus, e.g. an elongate parabolic mirror.

We claim:

1. Fault detection apparatus for the surface of a flat article of the type having a series of grooves which extend at least substantially parallel to one another, the grooves configured to produce light diffraction with pronounced diffraction orders, the apparatus comprising:
    a laser for generating a laser beam;
    a first optical system including a rotating mirror wheel against which the laser beam is directed to produce a scanning laser beam, the scanning laser beam directed against the surface of the flat article at an acute angle to said surface to scan along a scanning line generally perpendicular to the grooves;
    a second optical system arranged to gather diffracted light from the surface of the flat article of the zero diffraction order and at least the first diffraction order;
    the ratio of the wavelength of the laser beam to a grid constant of the grooves in the surface of the flat article being chosen to generate at most zero, first and second diffraction orders; and
    a photoelectric receiving arrangement, including a separate photoreceiver for each diffraction order, for generating an error signal on the occurrence of deviation of the diffracted light from a normal value.

2. The apparatus of claim 1 further comprising:
    a polarizer arranged in the laser beam; and
    an analyzer arranged before only one of the photoreceivers.

3. The apparatus of claim 1 wherein the second optical system includes a single strip-like cylindrical mirror.

4. The apparatus of claim 2 wherein the second optical system includes a single strip-like cylindrical mirror.

5. The apparatus of claim 1 wherein the second optical system includes a strip-like cylindrical lens for each photoreceiver.

6. The apparatus of claim 1 wherein the photoreceiver for at least one of the diffraction orders higher than the zero diffraction order includes a row of photoreceiver elements which extends substantially parallel to the scanning line.

7. The apparatus of claim 2 wherein the photoreceiver for at least one of the diffraction orders higher than the zero diffraction order includes a row of photoreceiver elements which extends substantially parallel to the scanning line.

8. The apparatus of claim 1 wherein the cross-section of the scanning laser beam in a direction perpendicular to the grooves has an extent such that it extends over more than five grooves.

9. The apparatus of claim 8 wherein the scanning laser beam extends over ten to 20 grooves.

* * * * *